United States Patent [19]

Coates

[11] Patent Number: 5,290,933

[45] Date of Patent: * Mar. 1, 1994

[54] PHENYLPYRIMIDONE DERIVATIVES

[75] Inventor: William J. Coates, Welwyn Garden City, England

[73] Assignee: SmithKline & French Laboratories Limited, Welwyn Garden City, United Kingdom

[*] Notice: The portion of the term of this patent subsequent to Jun. 2, 2009 has been disclaimed.

[21] Appl. No.: 794,311

[22] Filed: Nov. 14, 1991

Related U.S. Application Data

[63] Continuation of Ser. No. 514,385, Apr. 25, 1990, abandoned.

[30] Foreign Application Priority Data

Apr. 26, 1989 [GB] United Kingdom ................ 8909558

[51] Int. Cl.$^5$ ............................................. C07D 239/22
[52] U.S. Cl. ....................................................... 544/319
[58] Field of Search ............................................. 544/319

[56] References Cited

U.S. PATENT DOCUMENTS

| | | | |
|---|---|---|---|
| 3,660,403 | 5/1972 | Shen et al. | 260/251 |
| 3,745,161 | 7/1973 | Shen et al. | 260/251 |
| 3,883,653 | 5/1975 | Barth | 424/251 |
| 4,031,093 | 6/1977 | Juby et al. | 260/251 |
| 4,082,751 | 4/1978 | Juby et al. | 260/256.4 |
| 4,209,623 | 6/1980 | Juby | 544/319 |
| 4,241,056 | 12/1980 | Wetzel et al. | 424/226 |
| 5,118,686 | 6/1992 | Coates et al. | 514/269 |

OTHER PUBLICATIONS

Juby et al., III J. Med. Chem. 1982, 25, 1145–1150.
Juby et al., IV J. Med. Chem., 1979, 22, 263.

*Primary Examiner*—Patricia L. Morris
*Attorney, Agent, or Firm*—Linda E. Hall; Stuart R. Suter; Edward T. Lentz

[57] ABSTRACT

This invention relates to phenylpyrimidone derivatives which have bronchodilator activity. A compound of the invention is N-methyl 1,6-dihydro-6-oxo-2-(2-propoxyphenyl)pyrimidine-5-carboxamide.

6 Claims, No Drawings

PHENYLPYRIMIDONE DERIVATIVES

This is a continuation of application Ser. No. 07/514,385 filed Apr. 25, 1990, now abandoned.

The present invention relates to phenylpyrimidone derivatives, pharmaceutical compositions containing them and a method of effecting bronchodilatation by administering them. The compounds of this invention are inhibitors of a calmodulin insensitive cyclic GMP phosphodiesterase and are of use in combatting such conditions where such inhibition is thought to be beneficial. They are bronchodilators and are therefore of use in combatting chronic reversible obstructive lung diseases such as asthma and bronchitis. Furthermore they are vasodilators and are therefore of value in combatting angina, hypertension and congestive heart failure. They are also of use in the treatment of gastrointestinal motility disorders, for example irritable bowel syndrome.

U.S. Pat. Nos. 3,660,403 and 3,745,161 disclose compounds of the general formula (A):

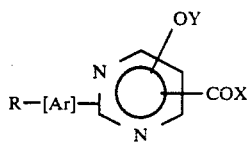
(A)

wherein COX and OY are ortho to each other and [Ar] is para to either COX or OY, R is inter alia lower alkoxy, [Ar] is inter alia phenyl, X is inter alia hydroxy, amino, alkylamino, dialkylamino or alkoxy, and Y is inter alia hydrogen. These compounds are described as having anti-inflammatory, anti-pyretic and analgesic activity. None of the compounds of the present invention are specifically disclosed.

U.S. Pat. No. 4,031,093 discloses anti-allergic compounds of the formula (B):

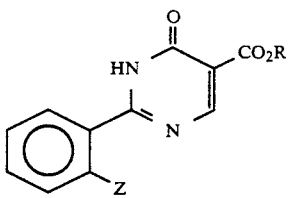
(B)

wherein Z is inter alia $C_{2-6}$alkoxy or $C_{2-6}$alkenyloxy and R is hydrogen or the residue of an easily cleavable ester group.

U.S. Pat. No. 4,082,751 discloses anti-allergic compounds of the formula (C):

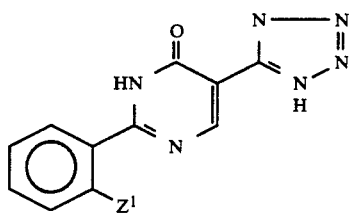
(C)

wherein $Z^1$ is inter alia lower alkoxy or lower alkenyloxy.

U.S. Pat. No. 4,082,751 also discloses intermediate compounds of the formula (D):

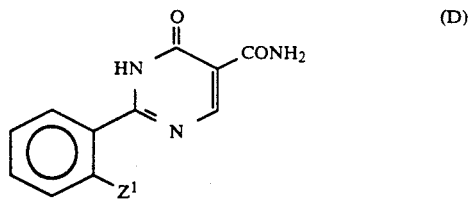
(D)

wherein $Z^1$ is as hereinbefore defined. In J. Med. Chem. 1982, 25, 1145-1150 it is indicated at page 1148 that the compounds of the formula (D) have insignificant antiallergic activity.

U.S. Pat. No. 4,241,056 discloses 3-(4-hydroxy-5-pyrimidyl)-ureido-penicillins. As intermediates for such compounds are described compounds of the general formula (E):

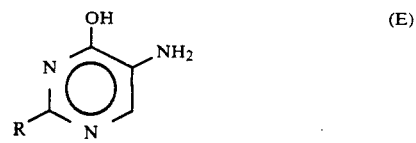
(E)

wherein R is inter alia phenyl optionally substituted by $C_{1-4}$alkoxy. None of the compounds of the present invention are specifically disclosed.

According to the present invention there is provided compounds of the formula (1):

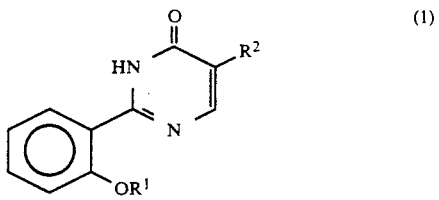
(1)

and pharmaceutically acceptable salts thereof, wherein $R^1$ is $C_{1-6}$alkyl, $C_{2-6}$alkenyl, $C_{3-5}$cycloalkyl$C_{1-6}$alkyl, phenyl$C_{1-6}$alkyl or $C_{1-6}$alkyl substituted by 1 to 6 fluoro groups; and $R^2$ is hydrogen, amino, —NHCOR$^3$, or -CONR$^4$R$^5$, wherein $R^3$ is $C_{1-6}$alkyl, $R^4$ is $C_{1-6}$alkyl and $R^5$ is hydrogen or $C_{1-6}$alkyl;

Suitably $R^1$ is $C_{2-5}$alkyl for example ethyl, n-propyl, isopropyl, butyl, isobutyl or pentyl.

Suitably $R^1$ is $C_{3-5}$alkenyl for example allyl, butenyl or pentenyl.

Suitably $R^1$ cyclopropylmethyl or benzyl.

Examples of $C_{1-6}$ is alkyl substituted by 1 to 6 fluoro groups include —CF$_3$, —CH$_2$CF$_3$ or —CF$_2$CHFCF$_3$.

Preferably $R^1$ is n-propyl.

Suitably $R^2$ is hydrogen, amino or —NHCOR$^3$ for example acetamido, propionamido or butyramido.

Suitably $R^2$ is —CONR$^4$R$^5$ for example N-methylcarboxamido, N-ethylcarboxamido or N,N-dimethylcarboxamido.

Specific compounds of this invention are:
N-methyl 1,6-dihydro-6-oxo-2-(2-propoxyphenyl)-pyrimidine-5-carboxamide,
N,N-dimethyl 1,6-dihydro-6-oxo-2-(2-propoxyphenyl)-pyrimidine-5-carboxamide, 5-amino-2-(2-propoxyphenyl)pyrimidin-4(3H)-one,
5-acetamido-2-(2-propoxyphenyl)pyrimidin-4(3H)-one,
or
2-(2-propoxyphenyl)pyrimidin-4(3H)-one,
or pharmaceutically acceptable salts thereof.

This invention covers all tautomeric and optical isomeric forms of compounds of formula (1).

Compounds of the formula (1) wherein $R^2$ is amino may form pharmaceutically acceptable salts with acids such as hydrochloric, hydrobromic, sulphuric and phosphoric acids.

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, sub-lingually, parenterally, transdermally, rectally, via inhalation or via buccal administration.

Compounds of formula (1) and their pharmaceutically acceptable salts which are active when given orally or via buccal administration can be formulated as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, celluloses, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil or solubilising agent, for example polyethylene qlycol, polyvinylpyrrolidone, 2-pyrrolidone, cyclodextrin, leoithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base.

The daily dosage regimen for oral administration is suitably about 0.001 mg/Kg to 120 mg/Kg, of a compound of formula (I) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calculated as the free base. The active ingredient may be administered as required for example from 1 to 8 times a day or by infusion. The compositions of the invention are bronchodilators and are useful in chronic reversible obstructive lung disease for example asthma and bronchitis. The compositions of the present invention are of use in the treatment of gastrointestinal motility disorders such as irritable bowel syndrome. The compositions of the present invention have vasodilator activity and are of use in the treatment of angina, hypertension and congestive heart failure. Such conditions can be treated by administration orally, sub-lingually, topically, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are bronchodilators such as sympathomimetic amines for example isoprenaline, isoetharine, sulbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) and pharmaceutically acceptable salts thereof can be prepared by a process which comprises reacting a compound of the formula (2):

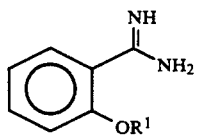

wherein $R^1$ is as hereinbefore defined; with a compound of the formula (3):

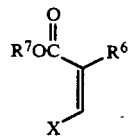

wherein X is a displaceable group, $R^6$ is a group $R^2$ as hereinbefore defined or a precursor thereof, and $R^7$ is an ester forming group, and thereafter where necessary: converting a group $R^6$ to a group $R^2$; optionally forming a pharmaceutically acceptable salt.

Suitably X is hydroxy or a derivative thereof, for example X is protected hydroxy such as silyloxy, an acid residue (for example $C_{1-6}$alkanoyloxy) or an ether residue (for example methoxy or ethoxy). Alternatively X is a secondary or tertiary amino group, for example di-$C_{1-6}$alkylamino such as dimethylamino or a cyclic amino group such as piperidino, pyrrolidino or morpholino. Preferably X is $C_{1-6}$alkoxy.

Suitably $R^7$ is $C_{1-6}$alkyl, for example methyl or ethyl.

Conveniently a solution of a compound of the formula (2) is initially formed by treatment of an acid addition salt of a compound of the formula (2) with a suitable base, for example a sodium alkoxide or sodium hydride in an organic solvent such as a $C_{1-4}$alkanol or dimethylformamide and the solution is then treated with a compound of the formula (3) at a moderate temperature, for example 0°–60° C., conveniently at ambient temperature. Suitable acid addition salts are those formed with inorganic acids such as hydrochloric or sulphuric acid or with strong organic acids such as methanesulphonic or p-toluene sulphonic acid.

An example of $R^6$ being a precursor to the group $R^2$ is when $R^6$ is a nitro group. Such a group can be reduced to an amino group in conventional manner, for example via catalytic hydrogenation, for example using hydrogen gas or catalytic transfer hydrogenation.

Compounds of the formula (1) wherein $R^2$ is amino can be converted to compounds of the formula (1) wherein $R^2$ is —$NHCOR^3$ by conventional methods of acylation, for example using an acid halide, an acid anhydride or an activated ester.

Alternatively $R^6$ is an ester group, such as $C_{1-6}$-alkoxycarbonyl, which can be converted to a —$CONR^4R^5$ group by reaction with an amine $R^4R^5NH$.

Compounds of the formula (1) wherein $R^2$ is hydrogen can be prepared by decarboxylating the corresponding compound wherein $R^2$ is carboxy, suitably prepared by hydrolysis of the corresponding compound wherein $R^2$ is an ester group, such as $C_{1-6}$alkoxycarbonyl.

Compounds of the formula (2) are known or preparable in conventional manner from U.S. Pat. No. 3,819,631.

Pharmaceutically acceptable acid addition salts of the compounds of the formula (1) wherein $R^2$ is amino may be prepared from the corresponding base of the compounds of the formula (1) in conventional manner. For example the base may be reacted with an acid in a $C_{1-4}$alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

In another aspect this invention provides a pharmaceutical composition comprising a pharmaceutically acceptable carrier and a compound of the formula (4) or a pharmaceutically acceptable salt thereof:

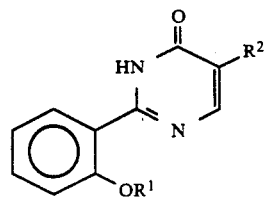

wherein $R^1$ is $C_{1-6}$alkyl, $C_{2-6}$alkenyl, $C_{3-5}$cycloalkyl$C_{1-6}$-alkyl, phsenyl$C_{1-6}$alkyl or $C_{1-6}$alkyl substituted by 1 to 6 fluoro groups, and $R^2$ is hydrogen, amino, —NHCOR$^3$ or —CONR$^4$R$^5$ wherein $R^3$ is $C_{1-6}$alkyl and $R^4$ and $R^5$ are independently hydrogen or $C_{1-6}$alkyl.

Specific compounds of the formula (4) are:
1,6-dihydro-6-oxo-2-(2-propoxyphenyl)pyrimidine-5-carboxamide,
N-methyl 1,6-dihydro-6-oxo-2-(2-propoxyphenyl)-pyrimidine-5-carboxamide,
N,N-dimethyl 1,6-dihydro-6-oxo-2-(2-propoxyphenyl)-pyrimidine-5-carboxamide,
5-amino-2-(2-propoxyphenyl)pyrimidin-4(3H)-one,
5-acetamido-2-(2-propoxyphenyl)pyrimidin-4(3H)-one, and
2-(2-propoxyphenyl)pyrimidin-4(3H)-one,
and pharmaceutically acceptable salts thereof.

The compounds of the formula (4) wherein $R^2$ is $CONH_2$ are known from U.S. Pat. No. 4,082,751. These compounds can be formulated as pharmaceutical compositions and used as medicaments in methods of therapy, as hereinbefore described for the compounds of formula (1).

The following biological test methods, data and Examples serve to illustrate this invention.

Bronchodilatation - In vivo

A. Male guinea-pigs of the Dunkin Hartley strain (500–600 g) were anaesthetised with Sagatal (pentobarbital sodium) (60 mg/kg i.p.). Airway resistance was measured using a modification of the classical Konzett-Rossler technique (J. Pharm. Methods, 13, 309–315, 1985). A dose of histamine which gave approximately 150% increase in airway resistance was selected for i.v. administration. Bolus doses of the compound under test were administered (i.v.) one minute before the histamine challenge and the subsequent peak inhibition of bronchoconstriction recorded.

The dose of compound required to reduce the histamine bronchoconstriction by 50% is given as the $BD_{50}$. These results demonstrate in-vivo anti-bronchoconstrictor activity.

| COMPOUND | $BD_{50}$ ($\mu$ mol/kg) |
| --- | --- |
| y | 5.6 |
| Ex 3 | 8.34 |
| Ex 4 | 8.4 |

Y = 1,6-dihydro-6-oxo-2-(2-propoxyphenyl)pyrimidine-5-carboxamide, (Preparation 44A of U.S. Pat. No. 4,082,751).

B. Male guinea-pigs of the Dunkin Hartley strain (500-600 g) were anaesthetised with Sagatal (pentobarbital sodium) (60 mg/kg). Airway resistance was measured using a modification of the classical Konzett-Rossler technique (J. Pharm. Methods, 13, 309-315, 1985). U46619 (9,11-methanoepoxy-PGH$_2$) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the U46619-induced bronchoconstriction by 50% is given as the $BD_{50}$. These results demonstrate in vivo anti-bronchoconstrictor activity.

| COMPOUND | $BD_{50}$ ($\mu$ mol/kg) |
| --- | --- |
| Ex 4 | 3.8 |
| Ex 5 | 3.2 |

Vasodilatation - In vivo

Male Wistar rats (300 g) were anaesthetised with a sodium 5-ethyl-5-(1-methylpropyl)-2-thiobarbiturate/sodium pentobarbitone mixture i.p. (62.5 and 22.5 mg/kg respectively). The trachea was cannulated and the rats breathed spontaneously air enriched with $O_2$ (5 ml/min). Blood pressure was recorded from a carotid artery and a jugular vein was cannulated for the administration of compounds. The temperature of the animal was maintained at 37° C. by the use of an electric blanket. The abdominal aorta was separated from the inferior veno cava, distal to the renal arteries and was cannulated centrally to supply the perfusion pump with blood and distally for the perfusion of the hind quarters at constant pressure. The perfusion circuit was primed with 5% bovine serum albumin dissolved in 0.9% sodium chloride solution, pH adjusted to 7.4. Initially the pump rate was set between 10 and 15 ml/min to match the hind quarter perfusion pressure to that of the systemic circulation. Once set, the pressure remained unaltered for the rest of the experiment. A change in the speed of the pump (equivalent to hindquarter blood flow) was used to assess the changes in hindquarter vascular resistance.

All compounds were administered as a bolus i.v. and from the dose response curves the dose required to produce a 50% increase in hindquarter blood flow ($EDHQ_{50}$) was determined in $\mu$moles/kg. The following results were obtained:

| COMPOUND | $EDHQ_{50}$ ($\mu$ mol/kg) |
| --- | --- |
| y | 23 |
| Ex 3 | 19 |
| Ex 4 | 15.8 |

-continued

| COMPOUND | $EDHQ_{50}$ ($\mu$ mol/kg) |
| --- | --- |
| Ex 5 | 22 | y is as hereinbefore defined.

EXAMPLE 1

N-Methyl 1,6-dihydro-6-oxo-2-(2-propoxyphenyl)-pyrimidine-5-carboxamide

Ethyl 1,6-dihydro-6-oxo-2-(2-propoxyphenyl)pyrimidine-5-carboxylate (1 g, U.S. Pat. No. 4,031,093) was treated with methylamine (33% in industrial methylated spirit, 50 ml) in a pressure vessel (379 kPa) at 120° C. for six hours and then allowed to cool. Solvent was removed under reduced pressure to afford a white solid which was triturated with ether, 0.88 g, m.p. 190°-191° C. This solid together with another sample prepared similarly (0.32 g) was recrystallised from ethanol to afford the title compound, 0.98 g, m.p. 192°-193° C.

Example 2

N,N-Dimethyl 1,6-dihydro-6-oxo-2-(2-propoxyphenyl)-pyrimidine-5-carboxamide

Ethyl 1,6-dihydro-6-oxo-2-(2-propoxyphenyl)pyrimidine-5-carboxylate (1.5 g, U.S. Pat. No. 4,031,093) was treated with dimethylamine (33% in industrial methylated spirit, 50 ml) in a pressure vessel (414 kPa) at 120° C. for 15 hours. Solvent was removed under reduced pressure affording a yellow oily residue which was washed several times with ether. The volume of the combined ethereal washings was reduced by evaporation to afford on standing overnight a white precipitate (540 mg). This was recrystallised from ether to afford the title compound, 310 mg, m.p. 104°-105° C.

EXAMPLE 3

5-Amino-2-(2-propoxyphenyl)pyrimidin-4(3H)-one a) Ethyl ethoxymethylene nitroacetate (15.76 g) was slowly added to a cooled (5° C.) solution of 2-propoxybenzamidine in ethanol (prepared from sodium, 1.92 g, in ethanol, 250 ml, and 2-propoxybenzamidine hydrochloride, 17.88 g). The reaction mixture was left overnight at ambient temperature and cooled at 0° C. for 3 days to afford the crude sodium salt of 5-nitro-2-(2-propoxyphenyl)-pyrimidin-4(3H)-one as a yellow solid, 4.10 g. A sample of the sodium salt (2.75 g) was dissolved in boiling water and 2 Normal hydrochoric acid was added which caused the precipitation of 5-nitro-2-(2-propoxyphenyl)pyrimidin-4(3H)-one, 2.60 g, m.p. 184°-186° C. A sample recrystallised from ethanol had m.p. 183°-184° C.

b) A mixture of 5-nitro-2-(2-propoxyphenyl)-pyrimidin-4(3H)-one (4.34 g) in methanol (120 ml) was treated with hydrogen at atmospheric pressure and ambient temperature in the presence of 10% palladium on carbon (170 mg) for five hours. The reaction mixture was filtered and the filtrate was evaporated under reduced pressure affording a dark oily residue. This was eluted from a silica column with chloroform and the combined fractions containing product were evaporated under reduced pressure to afford the crude title compound as a dark yellow solid, 1.69 g. This was recrystallised from isopropylacetate, then dissolved in boiling 2 Normal hydrochloric acid, and the filtered, cooled solution was washed with chloroform. The acidic solution was neutralised with potassium carbonate which afforded a pale yellow solid, 600 mg, which was recrystallised from acetonitrile to afford the title compound, 250 mg, m.p. 157°-158° C.

EXAMPLE 4

5-Acetamido-2-(2-propoxyphenyl)pyrimidin-4(3H)-one

A solution of 5-amino-2-(2-propoxyphenyl)pyrimidin-4(3H)-one (0.90 g) and 10 drops of acetic anhydride in acetic acid (50 ml) was heated on a steam bath for 4 hours. A further 10 drops of acetic anhydride was added and heating was continued for one hour. Acetic acid was removed under reduced pressure and water was added to the residue which afforded a light brown solid, 0.87 g. This was recrystallised from isopropylacetate to give the title compound, 0.32 g, m.p. 195°-197° C.

EXAMPLE 5

2-(2-Propoxyphenyl)pyrimidin-4(3H)-one

5-Carboxy-2-(2-propoxyphenyl)pyrimidin-4(3H)-one (2.03 g, U.S. Pat. No. 4,031,093) in quinoline (10 ml) was heated under reflux under nitrogen for two hours. Ether was added to the cooled reaction mixture which was then extracted with aqueous sodium hydroxide. The basic extract was washed with ether and then acidified with concentrated hydrochloric acid to pH 7. The aqueous mixture was extracted with chloroform and the chloroform extract was washed with aqueous hydrochloric acid, dried and evaporated under reduced pressure to afford a yellow solid. This solid was dissolved in ethanol and the ethanolic solution Was treated with charcoal, filtered and reduced in volume. From this precipitated a yellow solid impurity which was removed by filtration. A small quantity of the crude title compound (0.1 g) precipitated from the filtrate, however this together with another sample of crude title compound (0.54 g) similarly prepared was combined with the filtrate and eluted from a silica column with chloroform. Combined fractions containing product were evaporated under reduced pressure to afford a solid, 270 mg, which was recrystallised from ether to afford the title compound, 170 mg, m.p. 112°-113° C.

EXAMPLE 6

Pharmaceutical compositions for oral administration are prepared by combining the following:

| | % w/w | | |
|---|---|---|---|
| 5-Acetamido-2-(2-propoxyphenyl)pyrimidin-4(3H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 7

A pharmaceutical composition for parenteral administration is prepared by dissolving the title compound of Example 5 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

What is claimed is:

1. A compound of the formula (1):

$$\text{(1)}$$

or a pharmaceutically acceptable salt thereof, wherein $R^1$ is $C_{1-6}$alkyl, $C_{2-6}$alkenyl, $C_{3-5}$cycloalkyl$C_{1-6}$alkyl, phenyl$C_{1-6}$alkyl or $C_{1-6}$alkyl substituted by 1 to 6 fluoro groups; and $R^2$ is hydrogen, —NHCOR$^3$, or —CONR$^4$R$^5$, wherein $R^3$ is $C_{1-6}$alkyl, $R^4$ is $C_{1-6}$alkyl and $R^5$ is hydrogen or $C_{1-6}$alkyl.

2. A compound according to claim 1 wherein $R^1$ is $C_{2-5}$alkyl.

3. A compound according to claim 1 wherein $R^1$ is n-propyl.

4. A compound according to claim 1 wherein $R^2$ is hydrogen or —NHCOR$^3$.

5. A compound according to claim 1 wherein $R^2$ is —CONR$^4$R$^5$.

6. A compound according to claim 1 which is:
N-methyl 1,6-dihydro-6-oxo-2-(2-propoxyphenyl)-pyrimidine-5-carboxamide,
N,N-dimethyl 1,6-dihydro-6-oxo-2-(2-propoxyphenyl)-pyrimidine-5-carboxamide,
5-acetamido-2-(2-propoxyphenyl)pyrimidin-4(3H)-one, or
2-(2-propoxyphenyl)pyrimidin-4(3H)-one,
or a pharmaceutically acceptable salt thereof.

* * * * *